(12) United States Patent
Zanon et al.

(10) Patent No.: US 6,206,871 B1
(45) Date of Patent: Mar. 27, 2001

(54) SURGICAL KIT FOR IMPLANTATION OF AN INJECTION SITE

(76) Inventors: Claudio Zanon, Via Principessa Felicita di Savoia 13, 10131 Torino (IT); Maurizio Grosso, Regione Borgiona 52, 10090 Rivalba (Torino) (IT)

(*) Notice: Subject to any disclaimer, the term of this patent is extended or adjusted under 35 U.S.C. 154(b) by 0 days.

(21) Appl. No.: 09/214,367
(22) PCT Filed: May 27, 1997
(86) PCT No.: PCT/EP97/02732
§ 371 Date: Jan. 5, 1999
§ 102(e) Date: Jan. 5, 1999
(87) PCT Pub. No.: WO98/01182
PCT Pub. Date: Jan. 15, 1998

(30) Foreign Application Priority Data

Jul. 8, 1996 (IT) .............................................. TO96A0582

(51) Int. Cl.[7] ...................................................... A61K 9/22
(52) U.S. Cl. ........................................ 604/891.1; 604/131
(58) Field of Search ...................... 604/891.1, 131–134, 604/244, 175, 183–185, 264, 280–202; 606/1

(56) References Cited

U.S. PATENT DOCUMENTS

| 4,345,606 | | 8/1982 | Littleford . | |
|---|---|---|---|---|
| 4,685,905 | | 8/1987 | Hedwig . | |
| 5,078,702 | * | 1/1992 | Poneranz | 604/280 |
| 5,158,543 | | 10/1992 | Lazarus . | |
| 5,211,644 | * | 5/1993 | Vanbeek et al. | 606/1 |
| 5,476,452 | | 12/1995 | Thompson . | |
| 5,476,460 | * | 12/1995 | Montalvo | 604/891.1 |
| 5,620,419 | * | 4/1997 | Lui et al. | 604/116 |

* cited by examiner

*Primary Examiner*—Jennifer Maynard
(74) *Attorney, Agent, or Firm*—Sughrue, Mion, Zinn, Macpeak & Seas, PLLC

(57) ABSTRACT

The kit enables performing percutaneous connection between an arterial catheter (1) to be inserted along an artery leading to the region to be treated, and an infusion port (2) to be implanted in correspondence of a subcutaneous pocket-like cut (T) formed at a short distance from the opening (C) for introducing the catheter (1). The kit comprises a tunnelling assembly including a cannula needle (3) formed by a metal tubular inner stylet (4) having a tapered and bevelled tip (5) and by an outer jacket (6), a metal guide member (7), and a tunneler device (8) formed by an inner tubular dilator (9) and by an outer tubular introduction element (10) having a slightly tapered distal end (11) and a slightly countersunk proximal end (12).

2 Claims, 2 Drawing Sheets

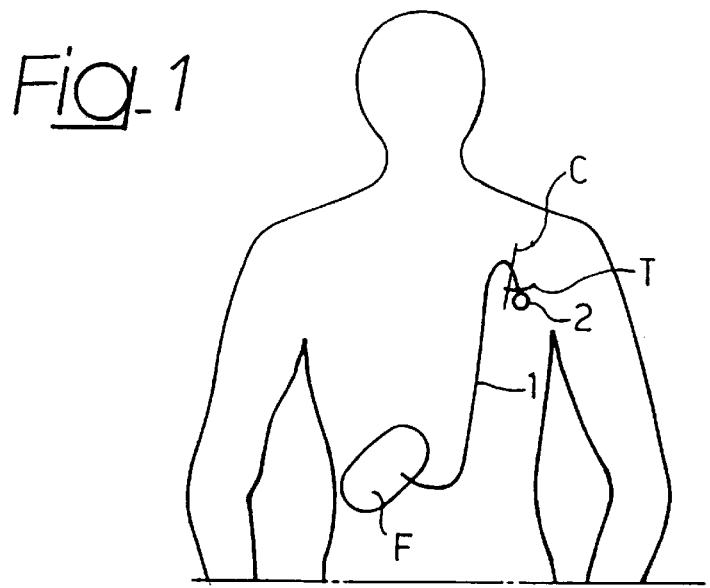
Fig. 1
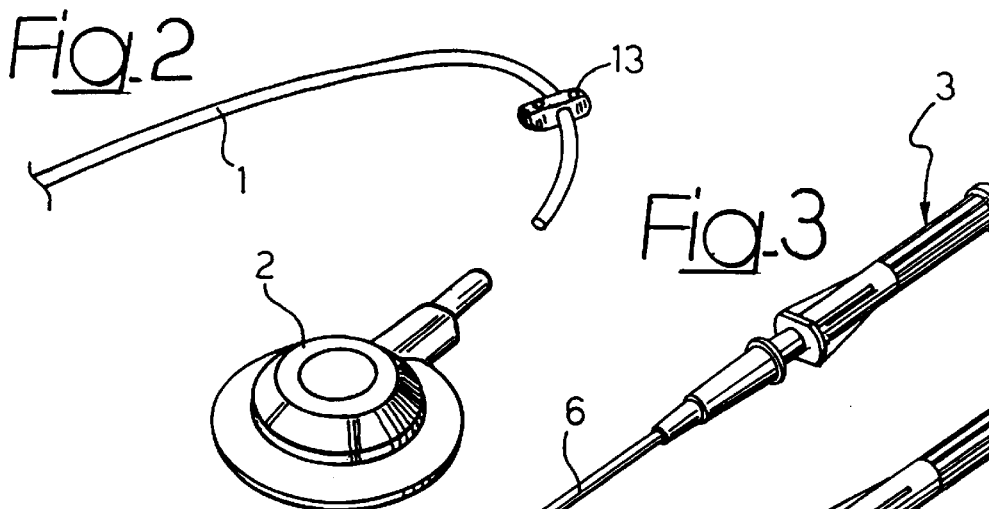
Fig. 2
Fig. 3
Fig. 4

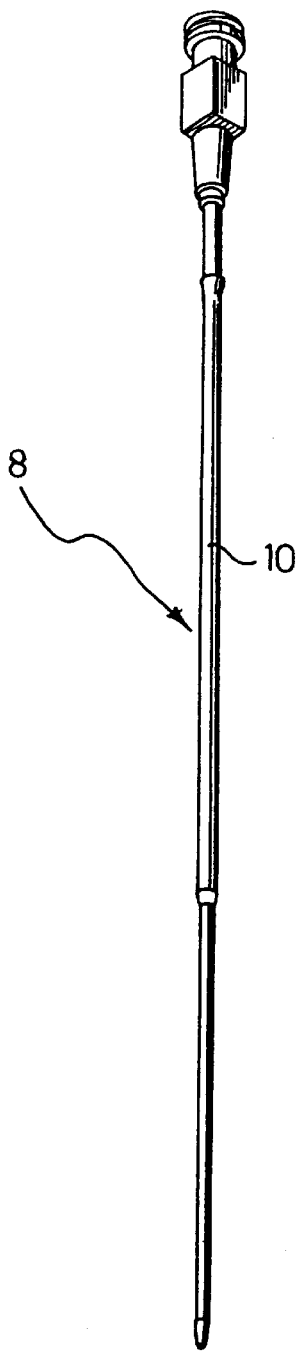
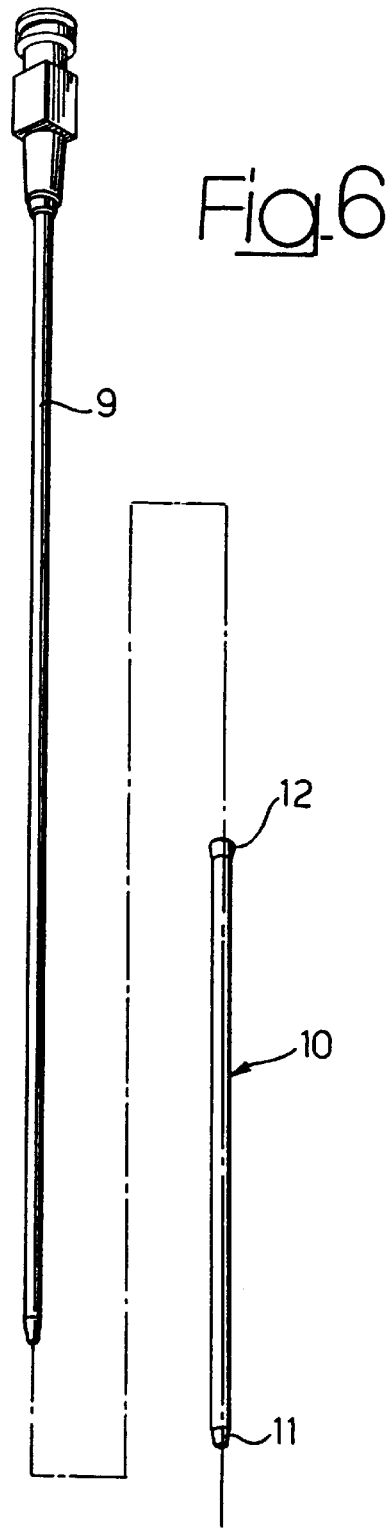
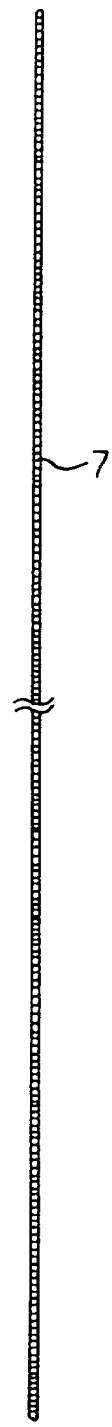

SURGICAL KIT FOR IMPLANTATION OF AN INJECTION SITE

TECHNICAL FIELD

The present invention is generally related to locoregional chemotherapy treatments through percutaneous arterial approach at several body districts, with particular (but not exclusive) reference to hepatic metastases of colon-rectal tumors.

State of the Prior Art

Locoregional chemotherapy of the hepatic metastases (Hepatic Artery Infusion—HAI) of the colon-rectal carcinoma started at the beginning of the 50's, with surprising results in terms of response to systemic chemotherapy. Case survey in this connection however did not reveal a sure gain in terms of patient surviving. On the other hand, recent clinical studies with new therapeutical protocols and novel proposals to employ HAI as adjuvant or neo-adjuvant both in surgical and in cryosurgical treatments, set again interests and hopes towards this kind of neoplasm treatment, and particularly of the hepatic metastases of the colon tumor.

One of the most relevant obstacles in connection with employing HAI is due to the fact that in the case of metachronous metastases (which are predominant), locoregional chemotherapy can be solely carried out by performing a further surgical operation, consisting of isolating the gastro-duodenal artery and joining up the port catheter into the hepatic artery, and subsequently creating a subcutaneous pocket housing the port itself. This surgical operation is not well accepted by the patients and additionally, in case of thrombosis or catheter displacement or infection, etc. the catheter itself can no longer be used and generally cannot be replaced.

More recent methodologies provide, instead of the above surgical operation, a day-hospital implantation method involving access through the left axillary artery and use of a subcutaneous port, under local anaesthesia. In case of occlusion, failure, displacement or infection, the catheter can be readily replaced so as to prosecute the HAI treatment.

Statement of the Invention

The present invention is related to a kit for performing the above disclosed methodology, i.e. implantation of a percutaneous arterial system for locoregional chemotherapy treatments of hepatic metastases, and more generally of tumors at several body districts such as vesica, pancreas, kidney, etc.

The kit according to the invention is essentially characterized in that it comprises:
- an arterial catheter made of a non-thrombogenic material and having a substantial length, to be inserted along an artery leading to the region to be treated, through an introduction opening,
- an infusion port to be implanted in correspondence of a subcutaneous pocket like cut formed at a short distance from said introduction opening of the catheter,
- a tunnelling assembly to perform percutaneous connection between said arterial catheter and said infusion port, including a cannula needle formed by a metal tubular inner stylet having a tapered and bevelled tip and by an outer jacket made of plastic material and adapted to be axially withdrawn from the inner stylet; a metal guide member to be inserted through said outer jacket of the cannula needle; and a tunneler device formed by an inner tubular dilator made of plastic material and by an outer tubular introduction element made of plastic material, having a slightly tapered distal end and a slightly countersunk proximal end, and relatively to which said inner dilator can be axially withdrawn.

BRIEF DESCRIPTION OF THE DRAWINGS

The invention further provides peculiar dimensional parameters of the kit as set forth in the above, which shall be disclosed in better detail in the following, with reference to the accompanying drawings purely provided by way of non limiting example, in which:

FIG. 1 is a diagrammatic view generally depicting the implantation mode, by means of a kit according to the invention, of an arterial system for locoregional chemotherapy treatment of hepatic metastases, FIG. 2 is a diagrammatic and partial view of a first and a second components of the kit, together with a third optional component, FIG. 3 is a diagrammatic perspective view showing a forth component of the kit according to the invention, FIG. 4 is an exploded view of FIG. 3, FIG. 5 is a diagrammatic perspective view showing a fifth component of the kit according to the invention, FIG. 6 is an exploded view of FIG. 5, and FIG. 7 is a diagrammatic elevational view of a sixth component of the kit according to the invention.

DETAILED DESCRIPTION OF THE INVENTION

The following description of the kit according to the invention is expressly referred to employ thereof for the percutaneous implantation of an arterial locoregional chemotherapy treatment system for hepatic metastases. Accordingly, the using mode of the kit will be expressly disclosed with reference to access through the left axillary artery of the patient: it is however to be pointed out that the kit according to the invention can be equally advantageously employed in connection with locoregional chemotherapy treatment of metastases at other body districts, possibly providing access through different arteries (for instance the femoral artery).

The components of the arterial system to be implanted are diagrammatically shown in FIG. 2: they include an arterial catheter 1, of a generally conventional type, having an outer diameter of about 6 F and an inner diameter of at least 1 mm. The catheter 1, made of a non-thrombogenic material (silicone, PTFE and the like), is however distinguished over the conventional catheters in that it has a substantial length, normally comprised between 50 and 100 mm.

The catheter 1 is intended to be inserted, through access via the left subclavian or axillary artery, along the hepatic artery so as to reach, with the distal end thereof, the liver F. The introduction mode of the catheter 1 shall be disclosed in more detail in the following.

The proximal end of the catheter 1 is intended to be connected to a conventional infusion port 2, preferably of the high-profile type, in turn adapted to be implanted in correspondence of a sub cutaneous pocket-like cut T formed at a short distance from the introduction opening or incision C for the catheter 1.

The kit according to the invention further comprises a tunnelling assembly, intended to enable percutaneous connection between the proximal end of the catheter 1 and the port 2, and the components of which, with reference to FIGS. 3 through 7, are the following:

- a cannula needle 3 formed by a metal tubular inner stylet 4 having a tapered and bevelled tip 5, and by an outer jacket 6 made of plastic material, which is axially fitted over the inner stylet 4 and can be axially withdrawn relative thereto; these components are generally conventional, but are however provided with peculiar dimensional parameters which shall be disclosed in the following;
- a metal guidewire 7, also generally conventional but having particular dimensional parameters;
- a tunneler device 8 formed by an inner tubular dilator 9 made of plastic material, and by an outer tubular introduction element 10, coaxially fitted within the tubular dilator 9 and adapted to be withdrawn therefrom. The introduction element 10 has a slightly tapered distal end 11 and a proximal end 12 which is slightly funnel-like countersunk.

An additional optional component of the kit according to the invention, also shown in FIG. 1, consists of a button-like subcutaneous retainer member 13, also generally conventional, which may possibly be employed for a more steady retention of the catheter 1 following positioning thereof.

Particular preferred dimensional parameters of the above-disclosed components of the kit according to the invention are listed herebelow:

- inner metal stylet 4 of the cannula needle 3: length substantially of 11 cm;
- outer jacket 6 of the cannula needle 3: length substantially of 10 cm, and inner diameter such as to allow passing the metal guidewire 7 therethrough;
- guidewire 7: length of about 50 cm, cross-section of 0.38;
- inner dilator 9 of the tunneler device 8: length of about 15 cm, outer diameter of about 6 F and inner diameter such as to allow passing the guidewire 7 therethrough;
- introduction element 10 of the tunneler device 8: length of about 10 cm.

It will be now briefly disclosed in the following the implantation method of the arterial system formed by the catheter 1 and port 2, in view of a chemotherapy treatment of metastases of the liver F.

Following local subclavicular anaesthesia, cut C is made and then the subclavian artery is punctured by means of a usual 18-gauge needle, through which a guidewire is introduced into the artery. The needle is then withdrawn, and a catheter is inserted over the guidewire by means of a proper introduction device, thus tubing the hepatic artery and the latter is removed so as to allow insertion of the catheter 1. The proximal end of the catheter 1, projecting for about 20 cm outside of the cut C, is then restrained by means of a conventional surgical forceps. Then the subcutaneous pocket-like incision T, into which the Port 2 is fitted, is made at a distance of 5–6 cm from the cut C.

Thereafter a tunnel is created between the cut C and the pocket T, firstly introducing the cannula needle 3, whose inner metal stylet 4 is subsequently withdrawn therefrom. The guidewire 7 is passed through the outer jacket 6 of the cannula needle 3, and then the outer jacket 6 is removed. The tunneler device 8 is introduced over the guidewire 7, and this guidewire 7 is then removed. The tubular dilator 9 of the tunneler device 8 is withdrawn, so as to allow introduction and passing the proximal end of the catheter 1 through the tubular introduction element 10. The proximal end of the catheter 1 is thus brought up to the pocket T, the tubular introduction element 10 is withdrawn, and lastly the end of the catheter 1 is cut at the desired length and connected to the port 2. The catheter 1 can thus be definitively fastened by means of the subcutaneous restraining member 13.

The operation so performed by means of the kit according to the invention can be carried out in a day-hospital fashion, and enables to immediately proceed with the chemotherapy treatment. In case of occlusion, failure, displacement or infection, the catheter 1 can be readily replaced, without any particular complications.

Naturally the details of construction and the embodiment can be widely varied with respect to what has been described and illustrated, without thereby departing from the scope of the present invention, such as defined in the appended claims.

What is claimed is:

1. A surgical method for percutaneous implantation of an arterial locoregional chemotherapy treatment system for metastases, comprising:
   - providing an arterial catheter (1) made of a non-thrombogenic material and having a substantial length, and inserting said arterial catheter along an artery leading to a region to be treated, through an introduction opening (C),
   - providing an infusion port (2) and implanting said infusion port in correspondence of a subcutaneous pocket-like cut (T) formed at a short distance from said introduction opening (C) of the arterial catheter,
   - providing a tunneling assembly including a cannula needle (3) formed by a metal tubular inner stylet (4) having a tapered and beveled tip (5) and by an outer jacket (6) made of plastic material and adapted to be axially withdrawn from said inner stylet (4);
   - a metal guide member (7) to be inserted through said outer jacket (6) of the cannula needle (3); and
   - a tunneller device (8) formed by an inner tubular dilator (9) made of plastic material and by an outer tubular introduction element (10) made of plastic material, having a slightly tapered distal end (11) and a slightly countersunk proximal end (12), and relatively to which said inner tubular dilator (9) has an outer diameter substantially equal to the outer diameter of said arterial catheter (1) so as to prevent displacement of said catheter when implanted, creating, through said tunneling assembly, a tunnel between said introduction opening and said pocket-like cut and performing, via said tunnel, percutaneous connection between said arterial catheter and said infusion port.

2. Method according to claim 1, further comprising providing a subcutaneous restraining member (13) of said arterial catheter (1) and implanting said restraining member in an area comprised between said introduction opening (C) and said pocket-like cut (T).

* * * * *